United States Patent
Lawson et al.

(10) Patent No.: US 6,592,857 B2
(45) Date of Patent: *Jul. 15, 2003

(54) TERTIARY AMIDE TERMINATED POLYAMIDES IN COSMETICS

(75) Inventors: Nelson E Lawson, Savannah, GA (US); Richard C MacQueen, Phillipsburg, NJ (US); Mark S Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/023,459

(22) Filed: Dec. 13, 2001

(65) Prior Publication Data

US 2003/0069388 A1 Apr. 10, 2003

Related U.S. Application Data

(63) Continuation-in-part of application No. 09/899,812, filed on Jul. 6, 2001, now Pat. No. 6,469,131, which is a continuation-in-part of application No. 09/225,889, filed on Apr. 1, 1999, now Pat. No. 6,268,466.

(51) Int. Cl.$^7$ ................................................ A61K 7/00
(52) U.S. Cl. ................................ 424/70.122; 424/70.1; 424/70.11; 424/70.17; 528/335
(58) Field of Search .......................... 424/70.122, 70.17, 424/70.1, 70.11; 528/335

(56) References Cited

U.S. PATENT DOCUMENTS

| | | | |
|---|---|---|---|
| 2,339,237 A | 1/1944 | Brubaker et al. | |
| 2,379,413 A | 7/1945 | Bradley | |
| 2,450,940 A | 10/1948 | Cowan et al. | |
| 2,662,068 A | 12/1953 | Floyd | |
| 2,861,048 A | 11/1958 | Wright et al. | |
| 3,141,787 A | 7/1964 | Goetze et al. | 106/252 |
| 3,148,125 A | 9/1964 | Strianse et al. | 167/85 |
| 3,156,572 A | 11/1964 | Carlick et al. | 252/316 |
| 3,341,465 A | 9/1967 | Kaufman et al. | 252/316 |
| 3,412,115 A | 11/1968 | Floyd et al. | 260/404.5 |
| 3,420,789 A | 1/1969 | Wilson | 260/18 |
| 3,595,816 A | 7/1971 | Barrett | 260/18 |
| 3,615,289 A | 10/1971 | Felton | 44/7.5 |
| 3,622,604 A | 11/1971 | Drawert et al. | 260/404.5 |
| 3,645,705 A | 2/1972 | Miller et al. | 44/7.5 |
| 3,819,342 A | 6/1974 | Gunderman et al. | 44/7.5 |
| 4,051,159 A | 9/1977 | Tsoucalas et al. | 260/404.5 |
| 4,062,819 A | 12/1977 | Mains et al. | 260/18 N |
| 4,128,436 A | 12/1978 | O'Hara et al. | 106/243 |
| 4,150,002 A | 4/1979 | Drawert et al. | 260/18 N |
| 4,259,183 A | 3/1981 | Cadotte | 210/654 |
| 4,275,054 A | 6/1981 | Sebag et al. | 424/65 |
| 4,337,298 A | 6/1982 | Karim et al. | 428/461 |
| 4,376,194 A | 3/1983 | Tanaka et al. | 528/288 |
| 4,438,240 A | 3/1984 | Tanaka et al. | 525/420 |
| 4,571,267 A | 2/1986 | Drawert et al. | 106/27 |
| 4,663,428 A | 5/1987 | Okitu et al. | 528/324 |
| 4,742,128 A | 5/1988 | Frisch et al. | 525/424 |
| 4,760,117 A | 7/1988 | Evans et al. | 525/394 |
| 4,769,285 A | 9/1988 | Rasmussen | 428/355 |
| 4,816,549 A | 3/1989 | Rumack | 528/336 |
| 4,946,922 A | 8/1990 | Reisch et al. | 528/76 |
| 5,102,656 A | 4/1992 | Kasat | 424/66 |
| 5,177,177 A | 1/1993 | Thullen et al. | 528/339.3 |
| 5,342,894 A | 8/1994 | Robeson et al. | 525/183 |
| 5,364,924 A | 11/1994 | Gerkin et al. | 528/73 |
| 5,372,852 A | 12/1994 | Titterington et al. | 427/288 |
| 5,432,204 A | 7/1995 | Farkas | 521/49 |
| 5,500,209 A | 3/1996 | Ross et al. | 424/66 |
| 6,268,466 B1 * | 7/2001 | MacQueen et al. | 528/335 |
| 6,469,131 B2 * | 10/2002 | Lawson et al. | 528/335 |

FOREIGN PATENT DOCUMENTS

GB 1129595 10/1968

* cited by examiner

Primary Examiner—Fred Zitomer
(74) Attorney, Agent, or Firm—Seed Intellectual Property Law Group PLLC

(57) ABSTRACT

A low molecular weight, tertiary amide terminated polyamide may be blended with a liquid hydrocarbon to form a transparent composition having gel consistency, and this gel may be used to formulate a cosmetic. The tertiary amide terminated polyamide may be prepared by reacting "x" equivalents of dicarboxylic acid wherein at least 50% of those equivalents are from polymerized fatty acid, "y" equivalents of diamine such as ethylene diamine, and "z" equivalents of a monofunctional reactant having a secondary amine group as the only reactive functionality. The stoichiometry of the reaction mixture is preferably such that $0.9 \leq \{x/(y+z)\} \leq 1.1$ and $0.1 \leq \{z/(y+z)\} < 0.7$. The gel contains about 5–50% tertiary amide terminated polyamide, with the remainder preferably being pure hydrocarbon.

40 Claims, 1 Drawing Sheet

TERTIARY AMIDE TERMINATED POLYAMIDES IN COSMETICS

CROSS-REFERENCE(S) TO RELATED APPLICATION(S)

This application is a continuation-in-part of U.S. patent application No. 09/899,812, filed Jul. 6, 2001, Pat. No. 6,469,131, which application is a continuation-in-part of U.S. patent application Ser. No. 09/225,889, filed Jan. 4, 1999, now U.S. Pat. No. 6,268,466, where these two applications are incorporated herein by reference in their entireties.

BACKGROUND OF THE INVENTION

1. Field of the Invention

This invention generally relates to cosmetics, and more particularly to cosmetics incorporating polyamide resins having tertiary amide termination.

2. Description of the Related Art

In many commercially important compositions, the consistency of the product is critical to its commercial success. One example is personal care products, which generally contain one or more active ingredients within a carrier formulation. While the active ingredient(s) determine the ultimate performance properties of the product, the carrier formulation is equally critical to the commercial success of the product in that it largely determines the consistency of the product. The rheology of the carrier (also referred to as the "base") largely determines the flow properties of the product, and the flow properties largely determine the manner in which the consumer will apply or use the product.

For example, aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate are metal salts that are commonly used as active ingredients in deodorant and antiperspirant products. Consumers have shown a preference for applying deodorant from a stick form. Thus, the carrier in a stick-form deodorant must be a relatively hard substance, and waxy fatty alcohol such as stearyl alcohol has often been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well-suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various Theological properties, in order to formulate a successful personal care product. Materials which have a gel-like character, in that they maintain their shape when undisturbed but flow upon being rubbed, are often desired for personal care products.

Transparent (i.e., clear) carriers are desired by formulators who develop a personal care product wherein colorant is an active ingredient, because a transparent carrier (as opposed to an opaque carrier) will minimally, if at all, interfere with the appearance of the colorant. In recent years, consumers have demonstrated an increasing preference for transparent and colorless personal care products such as deodorants and shampoos. There is thus an increasing demand for transparent materials which can provide the theological properties needed for various personal care products, and particularly which can impart gel-like character to a formulation.

Polyamide resin prepared from polymerized fatty acid and diamine is reported to function as a gellant in formulations developed for personal care products. For example, U.S. Pat. No. 3,148,125 is directed to a clear lipstick carrier composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Pure hydrocarbon is desirably included in personal care formulations because it is transparent and relatively inexpensive. Pure hydrocarbons are also available in a wide variety of viscosities and grades. However, pure hydrocarbon often does not have the Theological properties that are desired in a carrier, e.g., it does not naturally exhibit gel-like character. Furthermore, when hydrocarbon is present in a personal care formulation, alcohol is also typically present when a gel-like consistency is desired for the product. Alcohol can be irritating to skin, and accordingly, in some formulations, is desirably omitted.

Accordingly, there is a need in the art for cosmetic materials that have a gel-like consistency. The present invention provides this and related advantages as described herein.

SUMMARY OF THE INVENTION

In one aspect, the invention provides a cosmetic formulation that includes a tertiary amide terminated polyamide (ATPA) resin of the formula (1):

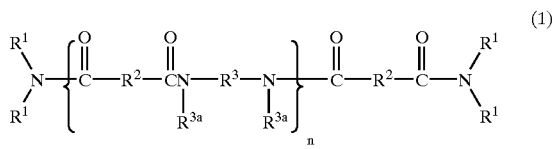

wherein, n designates a number of repeating units such that terminal amide groups (ie., the amide groups to which $R^1$ is directly bonded) constitute from 10% to 50% of the total amide groups of the ATPA;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$.

In another aspect, the invention provides a cosmetic formulation that includes an ATPA resin prepared by a method that includes reacting x equivalents of carboxylic acid from diacid or a reactive equivalent thereof, y equivalents of amine from diamine, and z equivalents of a secondary amine-containing molecule having no reactive functional groups except the secondary amine or a reactive equivalent thereof, where the secondary amine-containing molecule (i.e. monoamine) is substantially the only monofunctional reactant used to form the ATPA resin, and wherein each of x, y and z is greater than 0.

In another aspect, the invention provides a cosmetic composition that includes a low polarity liquid in addition to an ATPA resin as described above.

In another aspect, the invention provides a method for preparing a cosmetic composition, where the method includes combining a low polarity liquid with an ATPA resin as described above, and additional components as needed to prepare the specific cosmetic formulation.

These and other aspects of the present invention will become evident upon reference to the following drawing and detailed description.

DETAILED DESCRIPTION OF THE INVENTION

Figure 1:
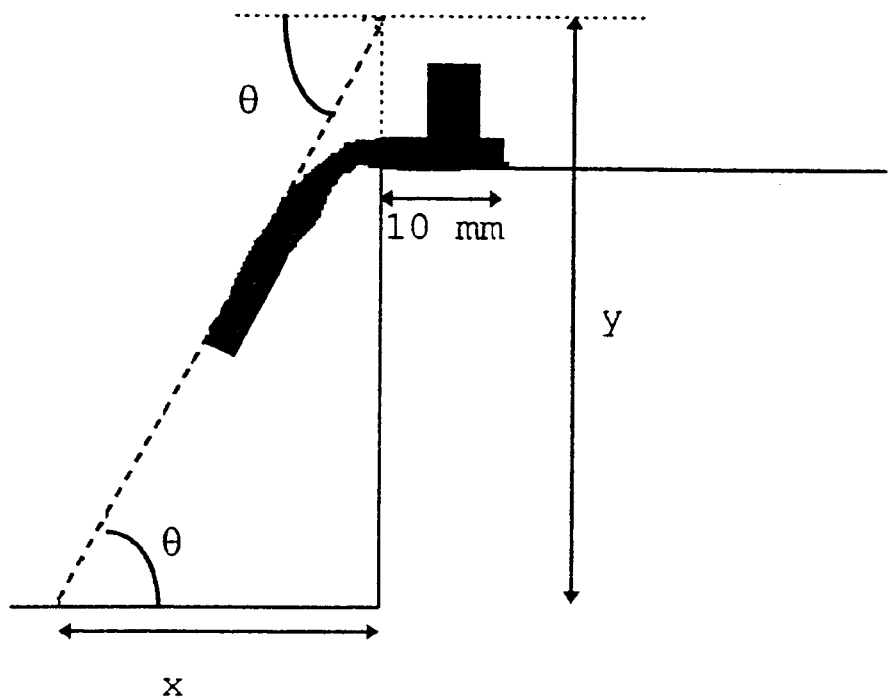
FIG. 1 illustrates a testing protocol for measuring the rigidity of a gelled sample.

In one aspect the present invention provides cosmetic formulations that include resins comprising short-chain polyamides of the formula (1), which will be referred to herein as tertiary amide terminated polyamides, or ATPAs.

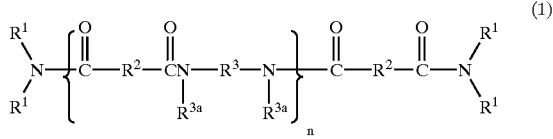

(1)

In formula (1), n designates a number of repeating units such that terminal (i.e., $R^1$-containing) amide groups constitute from 10% to 50% of the total of the amide groups shown in formula (1); $R^1$ at each occurrence is independently selected from a $C_{1-22}$ hydrocarbon group; $R^2$ at each occurrence is independently selected from a $C_{2-42}$ hydrocarbon group with the proviso that at least 50% of the $R^2$ groups have 30-42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

Preferably, the resin composition further comprises diamide having formula (1) wherein n=0, such that the ratio of terminal amide groups to the sum of amide groups in the total of the molecules that comprise the resin of formula (1) is from 0.1 to 0.7. Preferably, the resin composition is at reaction equilibrium.

As may be seen from formula (1), the ATPA resins have terminal amide groups of the formula —C(=O)N($R^1$)($R^1$) at both ends of a series of amide groups. These terminal amide groups are formed from secondary amines (since $R^1$ is an organic group and is not hydrogen), and therefore the terminal amide groups in formula (1) are properly referred to as tertiary amide groups. Accordingly, the ATPA resins may be referred to as tertiary amide terminated polyamides.

The letter "n" in formula (1) designates the number of repeating units present in a molecule of ATPA, and is an integer greater than 0. According to the invention, n may be 1, in which case the ATPA contains equal numbers of terminal amide and non-terminal amide groups, i.e., the terminal amide groups constitute 50% of the total of the amide groups in the ATPA molecule. The preferred ATPA resins are of relatively low molecular weight, so that n is preferably 1 to about 10, and more preferably is 1 to about 5. Because the ATPA molecules have such a low molecular weight, they could equally well be referred to as tertiary amide terminated oligoamides. In any event, viewed another way, the terminal amide groups constitute about 10% to about 50%, preferably about 15% to about 40%, and more preferably about 20% to about 35% of the total of the amide groups. A preferred ATPA resin includes a mixture of ATPA molecules of formula (1) having various n values. The ATPA resin has a weight average molecular weight of less than about 10,000, and typically less than about 5,000, but more than 500, typically more than 1,000, when measured by gel permeation chromatography using polystyrene calibration standards.

The $R^1$ group in formula (1) is a hydrocarbon group, and preferably is an alkyl or alkenyl group which contains at least 1, typically at least 4, and preferably more than 4 carbon atoms, e.g., 8, 10, 12, 14, 16, 18, 20, or 22 carbon atoms. Alkyl groups are preferred, however alkenyl groups having 1-3, and preferably 1 site of unsaturation are also suitable. The upper range for the number of carbon atoms in the $R^1$ group is not particularly critical, however preferably the $R^1$ group has less than or equal to about 22 carbon atoms. $R^1$ groups having about 16–22 carbon atoms are highly preferred. The identity of $R^1$ at any occurrence is independent of the identity of $R^1$ at any other occurrence.

Suitable $R^1$ groups are readily introduced into a molecule of formula (1) when secondary monoamine(s) is used as a co-reactant in preparing the ATPA resin. The secondary monoamine has the formula HN($R^1$)($R^1$), wherein $R^1$ is defined above. Suitable secondary monoamines are commercially available from a variety of sources, including Witco Corporation (Greenwich, Conn.; http://www.witco.com); Akzo Nobel Chemicals, Surface Chemistry (Chicago, Ill.; http://www.akzonobelusa.com); and Aldrich (Milwaukee, Wis.; http://Nvww.aldrich.sial.com). Ditallow amine is a preferred secondary monoamine.

The $R^2$ group in formula (1) is suitably a hydrocarbon containing 2 to 42 carbon atoms, and preferably contains 4 to 42 carbon atoms. A more preferred $R^2$ group contains 30-42 carbon atoms (i.e., is a $C_{30-42}$ group), and at least 50% of the $R^2$ groups in an ATPA resin preferably have 30–42 carbon atoms. Such $R^2$ groups are readily introduced into an ATPA when the resin is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^2$ groups is not readily available. However, good discussions of fatty acid polymerization may be found in, for example, U.S. Pat. No. 3,157,681 and *Naval Stores—Production, Chemistry and Utilization,* D. F. Zinkel and J. Russel (eds.), Pulp. Chem. Assoc. Inc., 1989, Chapter 23. Dimer acid is available commercially as, for example, UNIDYME™ dimer acid from Union Camp Corporation (Wayne, N.J.), EMPOL™ dimer acid from Henkel Corporation, Emery Oleochemicals Division (Cincinnati, Ohio); PRIPOL™ dimer acid from Unichema North America (Chicago, Ill.), and SYLVADYM™ dimer acid from Arizona Chemical, division of International Paper, (Panama City, Fla.).

While the preferred ATPA resins contain at least 50% $C_{30\text{-}42}$ groups as the $R^2$ group, more preferably the total of the $R^2$ groups consist of at least 75% $C_{30\text{-}42}$ groups, and still more preferably consist of at least 90% $C_{30\text{-}42}$ groups. ATPA resins of formula (1) wherein $R^2$ is entirely $C_{30\text{-}42}$ are preferred gelling agents of the invention.

However, ATPA resins may also contain $R^2$ groups having less than 30 carbon atoms. For example, an ATPA resin may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^2$ may be aliphatic or aromatic. When present, these lower carbon-number $R^2$ groups are preferably formed entirely of carbon and hydrogen, i.e., are hydrocarbyl groups. Such lower carbon-number $R^2$ groups preferably constitute less than 50% of the $R^2$ groups, however, when present, constitute about 1% to about 50%, and preferably about 5% to about 35% of the total of the $R^2$ groups. The identity of $R^2$ at each occurrence is independent of the identity of $R^2$ at any other occurrence. Suitable co-diacids are available from, for example, Aldrich (Milwaukee, Wis.).

The $—N(R^{3a})—R^3—N(R^{3a})—$ group in formula (1) links two carbonyl (C=O) groups. In a preferred embodiment of the invention, all of the $R^{3a}$ groups in an ATPA resin are hydrogen, so that $R^3$ alone joins the two nitrogen atoms shown in the formula $—N(R^{3a})—R^3—N(R^{3a})—$. In this case, the $R^3$ group contains at least two carbon atoms, and optionally oxygen and/or nitrogen atoms, in addition to any hydrogen atoms that are necessary to complete otherwise unfilled valencies of the carbon, oxygen and nitrogen atoms. In one embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ may contain aliphatic or aromatic structures. The identities of $R^3$ and $R^{3a}$ at each occurrence are independent of their identities at any other occurrence.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random, alternating or block) of ethylene oxide and propylene oxide. Such oxygenated $R^3$ groups are readily introduced into an ATPA resin through use of JEFFAMINE™ diamines (Huntsman Chemical, Inc., Houston, Tex.). These materials are available in a wide range of molecular weights, where any molecular weight diamine may be used in the preparation of the resins of the invention. While some of the $R^3$ groups may contain oxygen (at least about 1%), preferably a minor number (less than 50%) of the $R^3$ groups contain oxygen, and more preferably less than about 20% of the $R^3$ groups contain oxygen. The presence of oxygen-containing $R^3$ groups tends to lower the softening point of the ATPA resin.

When present, the nitrogen atoms in an $R^3$ group are preferably present as secondary or tertiary amines. A typical nitrogen-containing $R^3$ group having secondary amine groups is a polyalkylene amine, i.e., a group containing alternating alkylene groups and amine groups, which is sometimes referred to as a polyalkylene polyamine. The alkylene group is preferably a lower alkylene group, e.g., methylene, ethylene, (i.e., —CH$_2$CH$_2$—), propylene, etc. A typical polyalkylene amine may be represented by the formula $—NH—(CH_2CH_2NH)_m CH_2CH_2—NH—$ wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

wherein $R_c$ is a $C_{1\text{-}3}$ alkylene group.

In the above-described nitrogen-containing $R^3$ groups, $R^{3a}$ was hydrogen. However, $R^{3a}$ is not limited to hydrogen. In fact, $R^{3a}$ may be a $C_{1\text{-}10}$alkyl group, preferably a $C_{1\text{-}5}$alkyl group, and more preferably a $C_{1\text{-}3}$alkyl group. In addition, $R^3$ and $R^{3a}$, or two $R^{3a}$ groups, may together form a heterocyclic structure, e.g., a piperazine structure such as

In this case, the two $R^{3a}$ groups may be seen as joining together to form an ethylene bridge between the two nitrogen atoms, while $R^3$ is also an ethylene bridge. Additional suitable diamines are available from, for example, Aldrich (Milwaukee, Wis.).

The ATPA resin typically includes a mixture of ATPA molecules of formula (1) in addition to, for example, by-products that are formed during the ATPA-forming reaction. While the ATPA molecules of formula (1) may be purified from such by-products using, for example, chromatography or distillation, the by-products are typically either minimal in amount or impart desirable properties to the resin when the resin functions as a gelling agent, and thus need not be separated from the molecules of formula (1) in order for a suitable ATPA resin to be formed.

As described herein, amines and carboxylic acids are preferred starting materials to form the ATPA resins of the invention. These starting materials are preferably reacted together with a stoichiometry, and under reaction conditions, such that the acid number of the resulting ATPA resin is less than 25, preferably less than 15, and more preferably less than 10, while the amine number is preferably less than 10, more preferably less than 5, and still more preferably less than 1. The softening point of the ATPA resin is preferably greater than room temperature, more preferably is about 50° C. to about 150° C., and still more preferably is about 80° C. to about 130° C.

It is important to control the stoichiometry of the reactants in order to prepare an ATPA resin according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoamine has one equivalent of amine. Furthermore, it is emphasized that in preparing an ATPA resin, the diacid has only two reactive groups (both carboxylic acids), the monoamine has only one reactive group (a secondary amine group) and the diamine has only two reactive groups (preferably both primary amines), and these are preferably, although not necessarily, the only reactive materials present in the reaction mixture.

When co-diacid is employed to prepare an ATPA resin, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0-30 equivalent percent, and more preferably contributes 0-10 equivalent percent of the acid equivalents in the reaction mixture.

The stoichiometry of the reactants will have a significant impact on the composition of the ATPA resin. For example, ATPA resins made with increasing amounts of secondary monoamine will tend to have lower (number and weight) average molecular weights. In other words, as more mono-functional reactant is used, the number of amide pairs in an average molecule of formula (1) will decrease. On the other hand, as less monoamine is used, the average molecular weight of the molecules in the ATPA resin will increase. In general, increasing the average molecular weight of the ATPA will tend to increase the melting point and melt viscosity of the resin. When a high melting point ATPA is combined with a solvent to thereby form a gel, the gel will tend to have a firmer consistency than does a gel formed from an ATPA with a low melting point.

In order to prepare an ATPA resin, the above-described reactants (diacid, monoamine and diamine, or reactive equivalents thereof) may be combined in any order. Preferably, the reactants are simply mixed together and heated for a time and at a temperature sufficient to achieve essentially complete reaction, to thereby form the ATPA resin. During formation of the ATPA resin, the diacid and diamine groups will alternate to form what may be termed an alternating copolymer. The ATPA is not a block copolymer. The terms "complete reaction" and "reaction equilibrium" as used herein have essentially the same meaning, which is that further heating of the product gelling agent does not result in any appreciable change in the acid or amine numbers of the resin.

Thus, the ATPA resin may be formed in a one-step procedure, wherein all of the diacid (including co-diacid), secondary monoamine, and diamine are combined and then heated to about 180–250° C. for a few hours, typically 2–8 hours. When lower temperatures are used, a longer reaction time is typically needed to achieve complete reaction. When the reaction temperature is too high, the reactants and/or products may undergo undesirable thermally-induced decomposition. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the diacid, monoamine and diamine. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, dimer acid may be reacted with diamine so as to form polyamide, and then this intermediate polyamide may be reacted with monoamine to form a tertiary amide terminated dimer acid-based polyamide. Or, dimer acid may be reacted with the monoamine to thereby form diamide, and this diamide may be reacted with diamine to thereby form tertiary amide terminated dimer acid-based polyamide. Because the components of the ATPA resin are preferably in reaction equilibrium (due to transamidation), the order in which the reactants are combined typically does not impact on the properties of the gelling agent.

Any catalyst that may accelerate amide formation between carboxylic acid and amine groups may be present in the reaction mixture described above. Thus, mineral acid such as phosphoric acid, or tin salts such as dibutyltin oxide, may be present during the reaction. In addition, it is preferred to remove water from the reaction mixture as it is formed upon amide formation. This is preferably accomplished by maintaining a vacuum on the reacting mixture, or by passing a gentle stream of an inert gas (e.g., nitrogen) across the top of the reaction mixture.

The ATPA resins of the invention may be used to thicken and/or gel a solvent (where the term "a solvent" includes a mixture of solvents), and then this gelled solvent may be used in the preparation of a cosmetic. As used herein, the term solvent includes any substance which is a liquid at a temperature between 10–60° C., and which forms a gel upon being combined with an ATPA resin. As used herein, the term solvent will be used to encompass oils and other fluids which may be gelled by ATPA, and is not otherwise limited.

The combination of ATPA resin and solvent has a gel-like consistency. In general, materials which have a gel-like character will maintain their shape when undisturbed but flow upon being rubbed. Gels prepared with ATPA may be anywhere from soft to hard, where a "hard" gel has a rigid structure and is very resistant to deformation, while a "soft" gel exhibits some, but not too much, resistance to deformation. An illustration of "soft" gel may be seen in the preparation of Jell-O® dessert, which is a well known food product from Kraft Foods Inc. (division of Philip Morris Companies Inc., Northfield, Ill.). When prepared according to the package instructions, Jell-O® dessert is mixed with water to form a relatively soft gel.

The solvent may be a liquid or solid at room temperature, but is preferably a liquid. Examples of solvents that are solid at room temperature include fatty acids and fatty alcohols, such as myristic acid (flash point>159° C.) and myristyl alcohol (flash point >143° C.). A preferred solvent has a low polarity, where exemplary low polarity solvents include hydrocarbons and organic esters. The solvent may include minor amounts of co-solvents, such as alcohol (e.g., propylene glycol).

A preferred solvent is a hydrocarbon, where the hydrocarbon may be aliphatic or aromatic. A preferred hydrocarbon solvent is an oil, where mineral oil is a preferred oil. Mineral oils useful in the invention include, but are not limited to, transformer oil, spindle oil, cable insulating oil and machine oil. In one embodiment, the mineral oil is food grade mineral oil. Examples of suitable, commercially available mineral oils include SONNEBORN™ and CARNATION™ white oils from Witco Corp. (Greenwich, Conn.); ISOPAR™ K and ISOPAR™ H from Exxon Corp. (Houston, Tex.); and DRAKEOL™ and PENETECK™ white mineral oils from Penreco (Karns City, Pa.).

Other hydrocarbon solvents that may be used in the invention include relatively lower molecular weight hydrocarbons including linear saturated hydrocarbons such a tetradecane, hexadecane, octadecane, etc. Cyclic hydrocarbons such as decahydronaphthalene (DECALIN™), fuel grade hydrocarbons, branched chain hydrocarbons such as PERMETHYL™ from Permethyl Corp. and ISOPAR™ from Exxon Corp. (Houston, Tex.); and hydrocarbon mixtures such as product PD-23™ from Witco Corp. (Greenwich, Conn.) may also be used in preparing gels of the invention. Such hydrocarbons, particularly saturated hydrocarbon oils, are a preferred solvent for preparing a gel of the invention. Aromatic hydrocarbons, e.g., toluene or xylene, may also function as the solvent in a gel of the invention.

Another class of suitable solvents is esters. An ester will include the structural formula —C(=O)—O—, and preferably includes the structural formula —C(=O)—O—$R^5$ where $R^5$ is selected from $C_{1-C22}$ hydrocarbyl groups. As used herein, a hydrocarbyl group is formed exclusively from carbon and hydrogen. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, and triacontanyl stearate. Other suitable esters include glycerol and propylene glycol esters of fatty acids, including the so-called polyglycerol fatty acid esters and triglycerides.

Preferably, the solvent is a low-polarity liquid as described above, and more preferably the solvent is a liquid hydrocarbon. The liquid may contain more than one component, e.g., hydrocarbon as well as ester-containing material. In the mixture, the gellant (ATPA) typically contributes 10–95%, and the solvent typically contributes 5–90%, of the combined weight of the gellant and the solvent. Preferably, the gellant is combined with the solvent such that the weight percent of gellant in the gellant + solvent mixture is about 5–50%, and preferably is about 10–45%. Such gels may be transparent, translucent or opaque, depending on the precise identities of the gellant and solvent, as well as the concentration of gellant in the mixture.

In order to prepare a gel from a solvent and ATPA resin, the two components are mixed together and heated until homogeneous. A temperature within the range of about 80–150° C. is typically sufficient to allow the ATPA to completely dissolve in the solvent. A lower temperature may be used if a solution can be prepared at the lower temperature. Upon cooling, the mixture forms the gelled composition useful in the preparation of cosmetics of the present invention. Optional components having cosmetic appeal may be added to the molten composition, and are dispersed and/or dissolved to provide a homogeneous composition prior to cooling of the molten composition.

In one embodiment of the invention, the ATPA resin in combination with one or more solvents forms a rigid gel. As used herein, the term "rigidity" refers to the amount of deflection which a gel displays when responding to a force. More specifically, rigidity may be measured by holding a cylinder (or similar shape) of gel material in a horizontal direction. The extent to which the cylinder bends toward the earth under the force of gravity is used as a measure of the rigidity of the gel. A very rigid gel will not bend to any noticeable degree, while a gel that exhibits little or no rigidity will display considerable bend.

In order to impart quantitative meaning to the term "rigid", the test described below has been devised, which provides a measure of rigidity in terms of a "deflection value". The deflection values may range from a minimum of zero to a maximum of 90, where completely rigid material does not show any deflection and thus has a deflection value of zero, while a very flexible/limp material will show the maximum deflection and be described by a deflection value of 90.

The testing protocol is illustrated in FIG. 1. A gel sample having dimensions 57×10×3 mm is placed on a flat horizontal surface, such that 10 mm of the sample is on the surface and the remainder of the sample extends over the side of the surface and is unsupported. The degree to which the unsupported portion of the sample bends downward provides the deflection value. Thus, if the sample does not bend downward at all, it is assigned a deflection value of 0, because the unsupported portion is directed at an angle of 0° different from the supported portion of the sample. However, if the unsupported portion of the sample bends straight downward as soon as it is unsupported, then this sample has a deflection value of 90 because the unsupported and supported portions form a 90° angle with respect to each other. A material with a lower deflection value corresponds to a material with higher rigidity.

The ATPA-containing gels may have deflection values of less than or equal to 70, more preferably less than or equal to 60, still more preferably less than or equal to 50, yet more preferably less than or equal to 40, and still more preferably less than or equal to 30, yet still more preferably less than or equal to 20, further still more preferably less than or equal to 10, and further still more preferably less than or equal to 5, and most preferably equal to or essentially equal to zero.

In another embodiment, the ATPA gels may be formulated such that they are transparent. There are various degrees of transparency, ranging from crystal clear to hazy, which may be achieved with gels of the invention. In order to provide some measure of the absolute transparency of a gel, the following test has been devised. A white light is shined through a gel sample of a given thickness at room temperature, and the diffuse transmittance and the total transmittance of the light are determined. The percent haze for a sample is determined by the equation: %haze=(diffuse transmittance/total transmittance)×100. Samples are prepared by melting the gel (or product made therefrom) and pouring the melt into 50 mm diameter molds. The samples may be prepared at two thicknesses, e.g., 5.5±0.4 mm and 2.3±0.2 mm.

Clarity measurements are made on a Hunter Lab Ultrascan Sphere Spectrocolorimeter using the following settings: specular included, UV off, large area of view, illuminate D65, and observer 10°. Using this protocol with a 2.3 mm thickness sample, an ATPA gel of the present invention may have a %haze value of less than 75, while paraffin wax has a %haze value of over 90. The %haze value for a gel of the present invention can be increased if desired, by appropriate selection of solvent and gellant. Thus, the present invention provides gels (and articles made therefrom) having a transparency (measured by %haze) of less than 75, preferably less than 50, more preferably less than 25, still more preferably less than 10, and yet still more preferably of 5 or less.

In one embodiment, the ATPA gels are stable in that they do not display syneresis. As defined in the McGraw-Hill Dictionary of Scientific and Technical Terms (3rd Edition), syneresis is the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, syneresis is typically an undesirable property, and the ATPA gels desirably, and surprisingly do not exhibit syneresis. In one embodiment, the ATPA gels, and cosmetic articles prepared therefrom, may be stable in the sense that they do not exhibit syneresis. Thus, they do not have an oily feeling when handled.

The ATPA gels may be (although need not be) essentially transparent. When transparent, the gels may be combined with colorants (as well as other ingredients) to form lipstick or other cosmetic products, without the gel interfering with or tainting the appearance of the colorant. The ATPA gels may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories.

The cosmetic formulations of the present invention, which include ATPA and a gelled solvent, also may include one or more of the following: fragrance; antioxidant, such as vitamin E acetate; preservative; glitter; pigment and/or dye; glycerol triester such as glyceryl tricaprylate, glyceryl stearate, glyceryl caprate and/or glyceryl linoleate; aliphatic alcohol such as cetyl alcohol, stearyl alcohol and/or lanolin alcohol; fatty acid monoester such as laureth-2-octanoate, cetearyl octanoate, isopropyl palmitate and/or octyl palmitate; natural oil such as castor oil, sunflower oil and/or soybean oil; natural wax such as carnuba wax; fatty acid diester such as propylene glycol dicaprylate; filler such as silica; polyester such as polyglyceryl-3-diisotearate; silicone such as dimethicone; fatty acid such as stearic acid; and sunblock such as octyl methoxycinnamate and/or, octyl salicyclate; and alpha-hydroxy acids.

The cosmetic composition of the present invention may be in the form of a cream, or a stick, or it may be a pomade. The cosmetic composition may be formulated to function as a cuticle groomer, or a bath oil, or a massage oil, or a sunblock, or a makeup, or a lipstick, or a mascara.

Formulations to prepare such materials are well known in the art. For example, U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant. Other suitable cosmetic formulations are set forth in the Examples below.

The ATPA resin may be incorporated into cosmetic products such as those listed above by blending the ATPA resin with the other components of the product. In these commercial products, the ATPA resin will typically be present at a concentration of about 1% to about 50% of the composition, based on the total weight of the composition. It is a routine matter to optimize the amount of ATPA resin in a composition, and indeed the amount will vary depending on the actual product and the desired consistency of the product. In general, as more ATPA resin is used in a formulation, the product will display a more pronounced gel character, and will form a more rigid, or hard, gel. The following examples are offered by way of illustration and not by way of limitation.

EXAMPLES

In the following Examples, softening point was measured using a Model FP83HT Dropping Point Cell from Mettler Instruments, Mettler-Toledo International, Inc. (CH-8606 Greifensee, Switzerland; http://www.mt.com), with a heating rate of 1.5° C./min. Techniques to measure acid and amine numbers are well known in the art and need not be described here. See, e.g., ASTM D-465 (1982) from American Society for Testing and Materials (West Conshohocken, Pa.; http://www.astm.org).

In the following Examples, all chemicals used were of reagent grade unless noted otherwise, obtained from commercial supply houses such as Aldrich Chemical Co. (Milwaukee, Wis.). Ditallow amine, ethylene diamine, stearyl amine, and PD-23™ petroleum distillate were obtained from Witco Corporation (Greenwich, Conn.; hftp://www.witco.com). EMPOL™ 1008 polymerized fatty acid (a dimer acid), EMEREST™ 2452 polyglyceryl-3 diisostearate (diester), and CUTINA™ GMS stearic acid glyceryl monoester were obtained from Henkel Corporation (Ambler, Pa.; http://www.henkel.com). SYLVACLEAR™ A-200 tertiary amide-terminated polyamide resin was obtained from Arizona Chemical (Jacksonville, Fla.; http://www.arizona-chemical.com). CAPTEX™ 810D caprylic/capric/linoleic triglyceride, CAPTEX™ 200 propylene glycol dicaprylate/dicaprate (mixed diester), CAPTEX™ 1000 capric acid triglyceride, CAPTEX™ 350 caprylic/capric/lauric triglyceride, PURECO™ HOS sunflower oil, ABILATUM™ SC glycine soya oil (and) hydrogenated cottonseed oil, ACCONON™ CO-7 (PEG-7 glyceryl cocoate), ACCONON™ S-75 (PEG-75 soy glycerides), and CAPMUL™ GMS-50K stearic acid glyceryl monoester were obtained from Abitec Performance Products (Columbus, Ohio; http://www.abiteccorp.com). Isopropyl myristate (monoester) was obtained from Stepan Co. (Northfield, Ill.; http://www.stepan.com). Propylparaben (marketed under the name NIPASOL™ M) was obtained from Nipa Laboratories (Wilmington, Del.; http://www.nipa.com). CREMEROL™ HMG hydroxylated milk glycerides, AMERCHOL™ L-101 mineral oil (and) lanolin oil, GLUCAM™ P-20 PPG-20 methyl glucose ether, and SOLULAN™ C-24 choleth-24 (and) ceteth-24 mixed polyoxyethylene alcohol were obtained from Amerchol Corp. (Edison, N.J.). Octyl palmitate (monoester) was obtained from Goldschmidt Chemical Corp. (Hopewell, Va.). PROTACHEM™ IPM myristic acid isostearyl monoester, PROCOL™ PCA-10 PPG-10 cetyl ether, PROTACHEM™ AWS-100 PPG-5-ceteth-20 polyoxyethylene alcohol, PROCOL™ OA-2 SP oleth-2 polyoxyethylene alcohol, PROCOL™ OA-10 SP oleth-10 polyoxyethylene alcohol, PROTACHEM™ ISL linoleic acid isostearyl monoester, PROTACHEM™ CTG caprylic/capric triglyceride, PROTACHEM™ OS salicylic acid octyl monoester, PROTAPHENONE™-3 (benzophenone-3), and propylparaben were obtained from Protameen Chemicals Inc. (Totowa, N.J.; http://www.protameen.com). Octanoic acid laureth-2 polyoxyethylene monoester (marketed under the name HEST™ L-2-0) was obtained from Heterene Inc. (Paterson, N.J.; http://www.heterene.com). PERMETHYL™ 101A isohexadecane hydrocarbon, OMEGAPLANCTON™ caprylic/capric triglyceride, OLEAPHYCOL™ FV caprylic/capric triglyceride, PERMETHYL™ 102A isoeicosane hydrocarbon, SERICITE™ GMS-4C silica, and SPHERON™ N-2000 silica were obtained from Presperse Inc. (Piscataway, N.J.; http://www.presperse.com). Vitamin E (tocopherol) acetate, CREMOPHOR™ A6 (cetearath 6 mixed polyoxyethylene alcohol (and) stearyl monoalcohol), CREMOPHOR™ A25 (ceteareth 25 mixed polyoxyethylene alcohol), and LUVITOL™ EHO octanoic acid cetearyl mixed monoesters were obtained from BASF Corp. (Mt. Olive, N.J.; http://www.basf.com). Titanium dioxide 328™ was obtained from Whittaker, Clark, & Daniels, Inc. (S. Plainfield, N.J.; http://www.wcdinc.com). Iron oxide red 7080™, iron oxide yellow 7055™, and iron oxide black 7133™ were obtained from Warner Jenkinson (http://www.warner-jenkinson.com). FORAL™ 105 rosin ester was obtained from Hercules Inc. (Wilmington, Del.; http://www.herc.com). Octyl methoxycinnamate and butyl methoxydibenzoyl methane, sunscreen agents marketed as (respectively) PARSOL™ MCX and PARSOL™ 1789, were obtained from Givaudan (Teaneck, N.J.; http://www.givaudan.com). Silicon oil AK 500™ (dimethicone) was obtained from Wacker Silicones Corp. (Adrian, Mich.; http://www.wackersilicones.com).

Example 1

Tertiary Amide Terminated Polyamides (ATPA)

Several ATPA's (labeled ATPA A, B, and C) were made from the reactants, and relative amounts thereof, as set forth in Table 1. In Table 1, "DTA" is an abbreviation for di(hydrogenated tallow)amine, "EDA" is an abbreviation for ethylene diamine, "SA" is an abbreviation for stearyl amine, and PD-23™ is a petroleum distillate, all available from Witco Corporation (Greenwich, Conn.; http://www.witco.com). Selected properties for the ATPAs are also set forth in Table 1, including acid number, amine number, softening point ("S.P.") and the appearance when combined at 20 wt % solids in PD-23™ petroleum distillate ("Appearance").

In preparing ATPAs, a 60/40 EDA/DTA equivalent ratio results in a material (ATPA A) that forms a clear, hard gel in PD 23 distillate (at 20% solids). Increasing this ratio to 75/25 (see ATPA B) and 80/20 (see ATPA C) decreases the ATPA's solubility in PD-23™ petroleum distillate, resulting in opaque, hard gels.

TABLE 1

Properties of Tertiary Amide Terminated Polyamides

| ATPA | Composition (eq. %) | Acid No. | Amine No. | S.P. (° C.) | Appearance |
|---|---|---|---|---|---|
| A. | 100% EMPOL™ 1008; 60% EDA, 40% DTA | 20.8 | 25.1 | 82.2 | clear, hard gel |
| B. | 100% EMPOL™ 1008; 75% EDA, 25% DTA | 11.3 | 10.9 | 101.9 | opaque, hard gel |
| C. | 100% EMPOL™ 1008; 80% EDA, 20 DTA | 10.3 | 8.0 | 146.9 | opaque, hard gel |

Comparative Example 1

Secondary Amide Terminated Polyamide

As a comparative example, a polyamide at the same diamine/monoamine ratio as used in ATPA A (60/40, see Example 1) was prepared to determine if termination with a primary monoamine would result in polyamide that gelled hydrocarbons. This material, "Comp. A." was not compatible with PD-23™ petroleum distillate.

TABLE 2

Properties of Primary Amine-Terminated Polyamide

| Resin | Composition (eq. %) | Acid No. | Amine No. | S.P. (° C.) | Appearance |
|---|---|---|---|---|---|
| Comp. A. | 100% EMPOL™ 1008; 60% EDA, 40% SA | 5.5 | 0.9 | — | two phases |

Example 2

Formulation of Oil-based Pomade Gelled with ATPA

This example is directed to a process for forming a "Clear Mineral Oil Pomade."

A reaction vessel was charged with mineral oil and SYLVACLEAR™ A-200 tertiary amide-terminated polyamide resin according to the values indicated in Table 3, heated to about 105° C., agitated until homogeneous and clear, and cooled to about 80° C. Then, the esters isopropyl myristate and CAPTEX™ 810D caprylic/capric/linoleic triglyceride were charged to the vessel according to Table 3, with slow agitation, and cooled to 70° C. Then, cetyl alcohol and propylparaben were charged to the vessel according to Table 3, while color and fragrance were also charged to the vessel, in quantities appropriate to the weight percentages of the prior components. The mixture was stirred until homogeneous, and then poured into containers.

TABLE 3

Composition of Oil-Based Pomade Gelled with ATPA

| Component | Weight % |
|---|---|
| Mineral oil | 45.00 |
| SYLVACLEAR™ A-200 | 15.00 |
| CAPTEX™ 810D | 15.00 |
| Isopropyl myristate | 10.00 |
| Cetyl alcohol | 10.00 |
| Propylparaben | 0.10 |
| Color | q.s.* |
| Fragrance | q.s. |

*In sufficient quantity.

Example 3

Formulation of Oil-based Pomade Glitter Gelled with ATPA

This example is directed to a process for forming a "Clear Pomade Glitter for Body and Hair."

A reaction vessel was charged with mineral oil, isopropyl palmitate, and SYLVACLEAR™ A-200 tertiary amide-terminated polyamide resin according to the values indicated in Table 4, heated to about 105° C., agitated until homogeneous and clear, and cooled to about 80° C. Then, the remaining components (except the glitter) were charged to the vessel according to Table 4, with slow agitation until homogeneous, and cooled to 70° C. Then, glitter was charged to the vessel according to Table 4, and the mixture was stirred until the glitter was uniformly dispersed. The mixture was then poured into containers.

TABLE 4

Composition of Oil-Based Pomade Glitter Gelled with ATPA

| Component | Weight % |
|---|---|
| Mineral Oil | 40.00 |
| Isopropyl Palmitate | 25.00 |
| SYLVACLEAR ™ A-200 | 15.00 |
| tertiary amide-terminated polyamide | |
| CREMEROL ™ HMG | 7.00 |
| hydrogenated milk glycerides | |
| CAPTEX ™ 810D | 5.00 |
| caprylic/capric/linoleic triglyceride | |
| AMERCHOL ™ L-101 | 5.00 |
| mineral oil (and) lanolin oil | |
| GLUCAM ™ P-20 | 2.00 |
| PPG-20 methyl glucose ether | |
| SOLULAN ™ C-24 | 0.30 |
| choleth-24 (and) ceteth-24 mixed polyoxyethylene alcohol | |
| Glitter | 0.70 |

Example 4

Formulation of Oil-based Cuticle Groomer Gelled with ATPA

This example is directed to a process for forming a "Cuticle Groomer with Vitamin E."

A reaction vessel was charged with castor oil, PURECO™ HOS sunflower oil, and SYLVACLEAR™ A-200 tertiary amide-terminated polyamide resin according to the values indicated in Table 5, heated to about 105° C. under nitrogen, agitated until homogeneous and clear, and cooled to about 80° C. Then, the remaining components (except the Vitamin E acetate) were charged to the vessel according to Table 5, with slow agitation until homogeneous, and cooled to 70° C. Then, Vitamin E acetate was charged to the vessel according to Table 5, and the mixture was poured into containers.

TABLE 5

Composition of Oil-Based Cuticle Groomer Gelled with ATPA

| Component | Weight % |
|---|---|
| Castor Oil | 43.0 |
| PURECO ™ HOS | 16.0 |
| sunflower oil | |
| SYLVACLEAR ™ A-200 | 12.0 |
| tertiary amide-terminated polyamide | |
| CAPTEX ™ 810D | 7.0 |
| caprylic/capric/linoleic triglyceride | |
| ABI-LATUM ™ SC | 5.0 |
| glycine soya oil (and) hydrogenated cottonseed oil | |
| Cetyl alcohol | 5.0 |
| Octyl palmitate | 4.7 |
| CAPTEX ™ 200 | 4.0 |
| propylene glycol dicaprylate/dicaprate (mixed diester) | |
| Carnuba wax | 3.0 |
| Vitamin E acetate | 0.3 |

Example 5

Formulation of Bath Oil Gelled with ATPA

This example is directed to a process for forming a "Thick & Rich Bath Oil."

A reaction vessel was charged with mineral oil and SYLVACLEAR™ A-200 tertiary amide-terminated polyamide resin according to the values indicated in Table 6, heated to about 105° C., agitated until homogeneous and clear, and cooled to about 80° C. Then, the remaining components (except the fragrance) were charged to the vessel according to Table 6, with slow agitation until homogeneous, and cooled to 70° C. Then, fragrance was charged to the vessel according to Table 6, and the mixture was poured into containers.

TABLE 6

Composition of Bath Oil Gelled with ATPA

| Component | Weight % |
|---|---|
| Mineral Oil | 52.0 |
| SYLVACLEAR ™ A-200 | 5.0 |
| tertiary amide-terminated polyamide | |
| PROTACHEM ™ IPM | 12.0 |
| myristic acid isostearyl monoester | |
| PROCOL ™ PCA-10 | 12.0 |
| PPG-10 cetyl ether | |
| PROTACHEM ™ AWS-100 | 9.0 |
| PPG-5-ceteth-20 polyoxyethylene alcohol | |
| PROCOL ™ OA-2 SP | 4.0 |
| oleth-2 polyoxyethylene alcohol | |
| PROCOL ™ OA-10 SP | 3.0 |
| oleth-10 polyoxyethylene alcohol | |
| Fragrance | 3.0 |

Example 6

Formulation of Massage Oil Gelled with ATPA

This example is directed to a process for forming a massage oil.

A reaction vessel was charged with ingredients for creating Phase A, while another reaction vessel was charged with ingredients for creating Phase B (all according to the values indicated in Table 7). After heating both vessels to 85° C., the vessels were separated from the heat source, and the contents were combined with stirring. After cooling, perfume and preservatives were added in quantities appropriate to the weight percentages of the other components indicated in Table 7.

TABLE 7

Composition of Massage Oil Gelled with ATPA

| Component | Weight % |
|---|---|
| Phase A: | |
| PURECO ™ HOS | 53.5 |
| sunflower oil | |
| ABI-LATUM ™ SC | 8.0 |
| glycine soya oil (and) hydrogenated cottonseed oil | |
| CAPTEX ™ 1000 | 7.0 |
| capric acid triglyceride | |
| CAPTEX ™ 350 | 6.5 |
| caprylic/capric/lauric triglyceride | |
| SYLVACLEAR ™ A-200 | 9.0 |
| tertiary amide-terminated polyamide | |
| Stearyl alcohol | 4.0 |
| Cetyl alcohol | 1.5 |
| ACCONON ™ CO-7 | 4.0 |
| (PEG-7 glyceryl cocoate) | |
| ACCONON ™ S-75 | 1.5 |
| (PEG-75 soy glycerides) | |
| CAPMUL ™ GMS-50K | 1.0 |
| stearic acid glyceryl monoester | |
| Phase B: | |
| CAPTEX ™ 200 | 4.0 |

TABLE 7-continued

Composition of Massage Oil Gelled with ATPA

| Component | Weight % |
|---|---|
| propylene glycol dicaprylate/dicaprate (mixed diester) | |
| Other Ingredients: | |
| Perfume | q.s. |
| Preservatives | q.s. |

Example 7

Formulation of Sunblock Gelled with ATPA

This example is directed to a process for forming an "SPF-30 Face Stick" sunblock, in stick form.

A reaction vessel was charged with all ingredients (except fragrance) as indicated in Table 8. This mixture was heated to about 90° C. until melted and homogeneous, then was cooled to 75° C. before adding the fragrance.

TABLE 8

Composition of Sunblock Gelled with ATPA

| Component | Weight % |
|---|---|
| PROTACHEM ™ ISL | 10.00 |
| linoleic acid isostearyl monoester | |
| PROTACHEM ™ CTG | 25.00 |
| caprylic/capric triglyceride | |
| Mineral oil | 15.80 |
| Octylmethoxycinnamate | 7.50 |
| PROTACHEM ™ OS | 5.00 |
| salicylic acid octyl monoester | |
| Octocrylene | 8.00 |
| PROTAPHENONE ™-3 | 6.00 |
| (benzophenone-3) | |
| Propylparaben | 0.10 |
| SYLVACLEAR ™ A-200 | 22.00 |
| tertiary amide-terminated polyamide | |
| Fragrance | 0.60 |

Example 8

Formulation of Bath Oil Gelled with ATPA

This example is directed to a process for forming a "Blooming Bath Oil."

A reaction vessel was charged with HEST™ L-2-0 Octanoic acid laureth-2 polyoxyethylene monoester, PERMETHYL™ 101A isohexadecane hydrocarbon, and SYLVACLEAR™ A-200 tertiary amide-terminated polyamide, according to the values in Table 9, and heated to 100° C. until melted. The vessel was further charged with (in no particular order) Vitamin E acetate, OMEGAPLANCTON™ caprylic/capric triglyceride, and OLEAPHYCOL™ FV caprylic/capric triglyceride, according to Table 9, at 85° C. with mixing after each addition. Then, the vessel was further charged with fragrance according to Table 9, at 70° C. with mixing until clear.

TABLE 9

Composition of Bath Oil Gelled with ATPA

| Component | Weight % |
|---|---|
| HEST ™ L-2-0 | 40.00 |
| octanoic acid laureth-2 polyoxyethylene monoester | |
| PERMETHYL ™ 101A | 40.00 |
| isohexadecane hydrocarbon | |
| SYLVACLEAR ™ A-200 | 10.00 |
| tertiary amide-terminated polyamide | |
| Vitamin E Acetate | 0.50 |
| OMEGAPLANCTON ™ | 1.50 |
| caprylic/capric triglyceride | |
| OLEAPHYCOL ™ FV | 1.00 |
| caprylic/capric triglyceride | |
| Fragrance | 7.00 |

Example 9

Formulation of Makeup Gelled with ATPA

This example is directed to a process for forming a "Cream to Powder Anhydrous Makeup."

A reaction vessel was charged with ingredients to create Phase A (as indicated in Table 10), and heated to 100° C. with mixing until uniform. Another reaction vessel was charged with ingredients to create Phase B (as indicated in Table 10), mixed until uniform, then further pulverized until no discernible color streaks were observed. Another reaction vessel was charged with ingredients to create Phase C (as indicated in Table 10), and heated to 75° C. with mixing. Then, Phase A and Phase B were combined and mixed until uniform, at about 80° C. Then Phase C was added to the combined Phases A and B, mixed until uniform, and poured into containers at about 80° C.

TABLE 10

Composition of Makeup Gelled with ATPA

| Component | Weight % |
|---|---|
| Phase A: | |
| PERMETHYL ™ 102A | 24.00 |
| isoeicosane hydrocarbon | |
| SYLVACLEAR ™ A-200 | 8.00 |
| tertiary amide-terminated polyamide | |
| EMEREST ™ 2452 | 1.00 |
| polyglyceryl-3 diisostearate (diester) | |
| Phase B: | |
| SERICITE ™ GMS-4C | 10.00 |
| silica | |
| SPHERON ™ N-2000 | 30.00 |
| silica | |
| Titanium Dioxide 328 ™ | 6.00 |
| Iron Oxide Red 7080 ™ | 0.80 |
| Iron Oxide Yellow 7055 ™ | 0.60 |
| Iron Oxide Black 7133 ™ | 0.30 |
| Phase C: | |
| FORAL ™ 105 | 6.00 |
| rosin ester | |
| PERMETHYL ™ 102A | 13.30 |
| isoeicosane hydrocarbon | |

Example 10

Formulation of Cosmetic Cream Gelled with ATPA

This example is directed to a process for forming a "Protective Day Cream."

A reaction vessel was charged with ingredients to create Phase A (as indicated in Table 11), and heated to 100° C. with mixing until uniform. Another reaction vessel was charged with ingredients to create Phase B (as indicated in Table 11 and heated to 70° C. with mixing until uniform. Then, Phase A and Phase B were combined, cooled to 60° C., and mixed until homogeneous.

TABLE 11

Composition of Cosmetic Cream Gelled with ATPA

| Component | Weight % |
|---|---|
| Phase A: | |
| CREMOPHOR ™ A6 | 8.0 |
| (ceteareth 6 mixed polyoxyethylene alcohol (and) stearyl monoalcohol) | |
| CREMOPHOR ™ A25 | 7.0 |
| (ceteareth 25 mixed polyoxyethylene alcohol) | |
| LUVITOL ™ EHO | 25.0 |
| octanoic acid cetearyl mixed monoesters | |
| Mineral oil | 23.0 |
| SYLVACLEAR ™ A-200 | 10.0 |
| tertiary amide-terminated polyamide | |
| Cetyl alcohol | 5.0 |
| Phase B: | |
| CUTINA ™ GMS | 7.0 |
| stearic acid glyceryl monoester | |
| PARSOL ™ MCX | 6.0 |
| octyl methoxycinnamate sunscreen agent | |
| PARSOL ™ 1789 | 5.0 |
| butyl methoxydibenzoyl methane sunscreen agent | |
| Silicon Oil AK 500 ™ | 2.5 |
| (dimethicone) | |
| Fragrance | 1.5 |

All publications and patent applications mentioned in this specification are herein incorporated by reference to the same extent as if each individual publication or patent application was specifically and individually incorporated by reference.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A cosmetic comprising a tertiary amide terminated polyamide resin of the formula (1):

$$\underset{R^1}{\overset{R^1}{\diagdown}}N\left[\underset{}{\overset{O}{\underset{\|}{C}}}-R^2-\underset{}{\overset{O}{\underset{\|}{C}}}N-R^3-N\underset{R^{3a}}{\overset{}{\diagup}}\right]_n\underset{}{\overset{O}{\underset{\|}{C}}}-R^2-\underset{}{\overset{O}{\underset{\|}{C}}}-N\underset{R^1}{\overset{R^1}{\diagup}} \quad (1)$$

wherein, n designates a number of repeating units such that terminal amide groups constitute from 10% to 50% of the total amide groups;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$.

2. The cosmetic of claim 1 wherein terminal amide groups of the formula $C(=O)N(R^1)(R^1)$ constitute from 20% to 35% of the total of the amide groups.

3. The cosmetic of claim 1 wherein n is an integer from 1 to 5.

4. The cosmetic of claim 1 wherein $R^2$ is a $C_{30-42}$ hydrocarbon group having the structure of polymerized fatty acid with the carboxylic acid groups removed.

5. The cosmetic of claim 1 wherein between 1% and 50% of the $R^2$ groups are a $C_{4-19}$ hydrocarbon group.

6. The cosmetic of claim 1 wherein $R^3$ is a $C_{2-36}$ hydrocarbon group and $R^{3a}$ is hydrogen.

7. The cosmetic of claim 1 wherein at least 1% of the —N($R^{3a}$)—$R^3$—N($R^3$a)—groups are independently selected from polyalkylene amine, wherein $R_c$ is a $C_{1-3}$alkyl group.

8. The cosmetic of claim 1 further comprising diamide having formula (1) wherein n=0, such that the ratio of terminal amide groups to the total of the amide groups in the resin is from 0.1 to 0.7.

9. A cosmetic prepared from ATPA resin, the ATPA resin prepared by a method comprising reacting x equivalents of carboxylic acid from diacid or a reactive equivalent thereof, y equivalents of amine from diamine and z equivalents of a secondary amine-containing monoamine having no reactive functional groups except the secondary amine or a reactive equivalent thereof, where the monoamine is substantially the only monofunctional reactant used to form the resin, and wherein each of x, y and z is greater than 0.

10. The cosmetic of claim 9 wherein at least about 50% of the carboxylic acid equivalents are from polymerized fatty acid, $0.9 \leq \{x/(y+z)\} \leq 1.1$, and $0.1 \leq \{z/(y+z)\} \leq 0.7$.

11. The cosmetic of claim 9 wherein all equivalents of carboxylic acid come from polymerized fatty acid.

12. The cosmetic of claim 9 wherein the diamine has the formula $H_2N$—$R^3$—$NH_2$ and $R^3$ is a $C_{2-36}$ hydrocarbon group.

13. The cosmetic of claim 9 wherein at least 50% of the amine equivalents are contributed by a diamine of the formula $H_2N$—$R^3$—$NH_2$ wherein $R^3$ is a $C_{2-36}$ hydrocarbon group, and at least 1% of the amine equivalents are contributed by one or more diamines selected from and $H_2N$—$R^3$—$NH_2$, wherein $R^3$ is selected from polyalkylene oxide, polyalkylene amine, and the formula

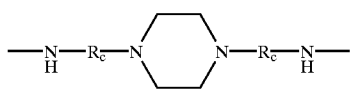

wherein $R_c$ is a $C_{1-3}$ alkyl group.

14. The cosmetic of claim 9 wherein the secondary amine-containing molecule has the formula $R^1$—NH—$R^1$, and $R^1$ is independently at each occurrence a $C_{12-22}$ hydrocarbon group.

15. A cosmetic of claim 1, further comprising fragrance.

16. A cosmetic of claim 1, further comprising an antioxidant.

17. A cosmetic of claim 16, wherein the antioxidant is Vitamin E acetate.

18. A cosmetic of claim 1, further comprising preservative.

19. A cosmetic of claim 1, in the form of a cream.

20. A cosmetic of claim 1, wherein said cosmetic is a pomade.

21. A cosmetic of claim 1, further comprising glitter.

22. A cosmetic of claim 1, wherein said cosmetic is a cuticle groomer.

23. A cosmetic of claim 1, wherein said cosmetic is a bath oil.

24. A cosmetic of claim 1, wherein said cosmetic is a massage oil.

25. A cosmetic of claim 1, wherein said cosmetic is a sunblock.

26. A cosmetic of claim 1 in the form of a stick.

27. A cosmetic of claim 1, wherein said cosmetic is makeup.

28. A cosmetic of claim 1, comprising pigment and/or dye.

29. A cosmetic of claim 1, comprising glyceryl tricaprylate, glyceryl stearate, glyceryl caprate and/or glyceryl linoleate.

30. A cosmetic of claim 1, comprising cetyl alcohol, stearyl alcohol and/or lanolin alcohol.

31. A cosmetic of claim 1, comprising isopropyl palmitate and/or octyl palmitate.

32. A cosmetic of claim 1, comprising castor oil, sunflower oil and/or soybean oil.

33. A cosmetic of claim 1, comprising carnuba wax.

34. A cosmetic of claim 1, comprising propylene glycol dicaprylate.

35. A cosmetic of claim 1, comprising laureth-2-octanoate and/or cetearyl octanoate.

36. A cosmetic of claim 1, comprising silica.

37. A cosmetic of claim 1, comprising polyglyceryl-3-diisotearate.

38. A cosmetic of claim 1, comprising dimethicone.

39. A cosmetic of claim 1, comprising stearic acid.

40. A cosmetic of claim 1, comprising octyl methoxycinnamate and/or, octyl salicyclate.

* * * * *

UNITED STATES PATENT AND TRADEMARK OFFICE
CERTIFICATE OF CORRECTION

PATENT NO. : 6,592,857 B2
DATED : July 15, 2003
INVENTOR(S) : Nelson E. Lawson et al.

It is certified that error appears in the above-identified patent and that said Letters Patent is hereby corrected as shown below:

<u>Title page,</u>
Item [63], the filing date for Application No. 09/225,889 should read as
-- January 4, 1999 --.

<u>Column 20,</u>
Lines 23 to 27, the first figure should appear as 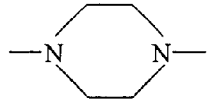

Signed and Sealed this

Twentieth Day of January, 2004

JON W. DUDAS
*Acting Director of the United States Patent and Trademark Office*